United States Patent [19]

Leifeld

[11] Patent Number: 4,839,943
[45] Date of Patent: Jun. 20, 1989

[54] APPARATUS FOR DETECTING FOREIGN BODIES IN A FIBER TUFT MASS

[75] Inventor: Ferdinand Leifeld, Kempen, Fed. Rep. of Germany

[73] Assignee: Trützschler GmbH & Co. KG, Mönchengladbach, Fed. Rep. of Germany

[21] Appl. No.: 134,869

[22] Filed: Dec. 18, 1987

[30] Foreign Application Priority Data

Dec. 24, 1986 [DE] Fed. Rep. of Germany ....... 3644535

[51] Int. Cl.⁴ .............................................. D01B 1/00
[52] U.S. Cl. .................................................... 19/80 R
[58] Field of Search ..................... 19/0.21, 0.22, 80 R, 19/81, 302

[56] References Cited

U.S. PATENT DOCUMENTS

| | | | |
|---|---|---|---|
| 2,427,435 | 9/1947 | Wollner | 356/433 |
| 3,781,150 | 12/1973 | Matsumura et al. | 19/302 X |
| 4,481,694 | 11/1984 | Dilo | 19/302 X |
| 4,510,646 | 4/1985 | Locatelli et al. | 19/80 R |
| 4,707,887 | 11/1987 | Leifeld et al. | 19/0.2 |

FOREIGN PATENT DOCUMENTS

| | | |
|---|---|---|
| 0000033 | 12/1978 | European Pat. Off. . |
| 0226430 | 6/1987 | European Pat. Off. . |
| 1648430 | 7/1971 | Fed. Rep. of Germany . |
| 2818310 | 11/1978 | Fed. Rep. of Germany . |
| 2021047 | 1/1987 | Japan .................................. 19/0.21 |
| 0154134 | 4/1932 | Switzerland . |
| 0576011 | 5/1976 | Switzerland . |
| 1211463 | 11/1970 | United Kingdom . |
| 1213781 | 11/1970 | United Kingdom . |
| 1443296 | 7/1976 | United Kingdom . |
| 1468895 | 3/1977 | United Kingdom . |
| 2032618 | 5/1980 | United Kingdom . |
| 2095828 | 10/1982 | United Kingdom . |

Primary Examiner—Werner H. Schroeder
Assistant Examiner—Sara M. Current
Attorney, Agent, or Firm—Spencer & Frank

[57] ABSTRACT

An arrangement for ascertaining the presence of foreign bodies in a mass of fiber tufts comprises a fiber tuft-supporting surface; a device for providing a loose fiber tuft layer on the tuft-supporting surface; a foreign body detecting apparatus arranged for scanning the fiber tuft layer for foreign bodies; and a moving device for effecting relative displacement between the fiber tuft layer and the apparatus.

17 Claims, 3 Drawing Sheets

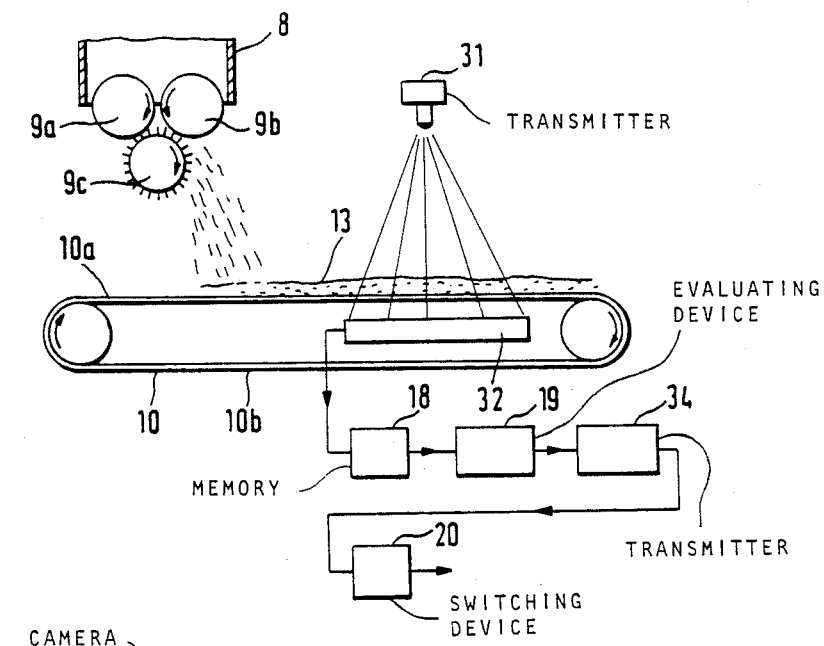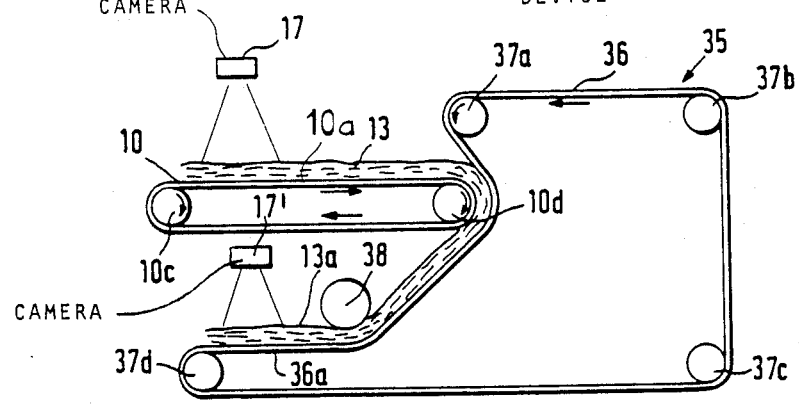

APPARATUS FOR DETECTING FOREIGN BODIES IN A FIBER TUFT MASS

BACKGROUND OF THE INVENTION

This invention relates to an apparatus for detecting foreign bodies such as foreign fibers, tying strings, bands of synthetic material, wire pieces and the like within or between textile fiber tufts, particularly cotton and/or synthetic fiber tufts.

In practice undesirable foreign fiber materials may be found within a cotton or synthetic fiber mass which, to a significant degree, adversely affect the making of high quality yarns. The foreign fiber material frequently remains in the mass of useful fibers after processing in the cleaning and spinning installations and, among others, disadvantageously leads to colorings. In many instances, the impurities are jute, kemp or polypropylene strings or bands. The foreign fibers originate mostly from packaging and from sacks which had been utilized during harvest.

Foreign fibers, tying strings or the like can be found in practice frequently in the pressed fiber bales. The pressed-in strings extend often through several layers (zones) so that it is frequently necessary to manually dig deeply into the bales for removing the entire string or band. Proceeding in this manner is very time-consuming and adversely affects the continuous fiber processing.

SUMMARY OF THE INVENTION

It is an object of the invention to provide an improved detecting apparatus which, in particular, makes possible a reliable spotting and simple removal of foreign bodies, particularly foreign fibers.

This object and others to become apparent as the specification progresses, are accomplished by the invention, according to which, briefly stated, the fiber tufts are arranged in a loose layer and a foreign body detecting device and the loose fiber tuft mass are moved relative to one another.

By providing a loose fiber tuft mass, the foreign bodies are not embedded firmly in the inside of the mass as it is the case in a pressed fiber bale but are arranged loosely within or between fiber tufts and, also because of the small height of the loose fiber layer, are easily detectable. Further, the foreign bodies are, because of the loose layer, easily accessible which makes possible a simple removal thereof.

The foreign bodies, particularly threads, strings and the like differ from the fiber tufts in that they are relatively long and slender. By virtue of the fact that the opened fiber tufts are arranged in a loose layer and that an apparatus is provided which can detect the foreign bodies, that is, the foreign bodies may be recognized from the exterior, there is achieved a reliable recognition so that a differentiation and removal of the foreign bodies from the fiber tufts is made possible. Preferably, a conveyor belt is provided on which the fiber tuft layer moves relative to the stationarily arranged detecting apparatus. Expediently, the conveyor belt is a sieve belt which is exposed to suction. According to a further feature of the invention a fiber tuft supplying device is arranged upstream of the conveyor belt. Preferably, the detecting device ascertains the configuration and/or the color and/or the size and/or the brightness of the foreign bodies. Advantageously, the detecting apparatus has a transmitted and a receiver for electromagnetic waves or rays. Expediently, the apparatus is a picture-taking device such as a television camera. Advantageously, the apparatus is an X-ray device. Preferably, an image memory receives signals from the detecting device. Preferably, an evaluating device receives signals from the image memory for distinguishing the foreign bodies from the fiber tufts. Expediently, downstream of the evaluating device there is arranged an apparatus for removing the foreign bodies. Expediently, between the evaluating device and the apparatus for removing the foreign bodies a switching device is arranged. Advantageously, the apparatus according to the invention is situated immediately downstream of the bale opener which removes fiber tufts from the textile fiber bales.

Expediently, the fiber tufts removed from the fiber bales by the bale opener are placed on a belt by an at least approximately uniform spreading operation. The belt may be a conveyor belt whereby a thin layer of fiber tuft mass may be obtained. Such thin layer is, during conveyance thereof, monitored by an optical system, for example, a camera. Pictures are produced which are electronically automatically evaluated with an image evaluating device for determining the presence of foreign bodies. After recognizing a foreign body such as a thread or an accumulation of threads, a removal apparatus at an accurately calculated distance from the locus of determination is activated which removes the material zone of the loose layer where the foreign body was found.

BRIEF DESCRIPTION OF THE DRAWING

FIG. 4 is a schematic side elevational view with a block diagram, showing another preferred embodiment of the invention.

FIG. 5 is a schematic side elevational view of a further preferred embodiment of the invention.

DESCRIPTION OF THE PREFERRED EMBODIMENTS

Figure 1:
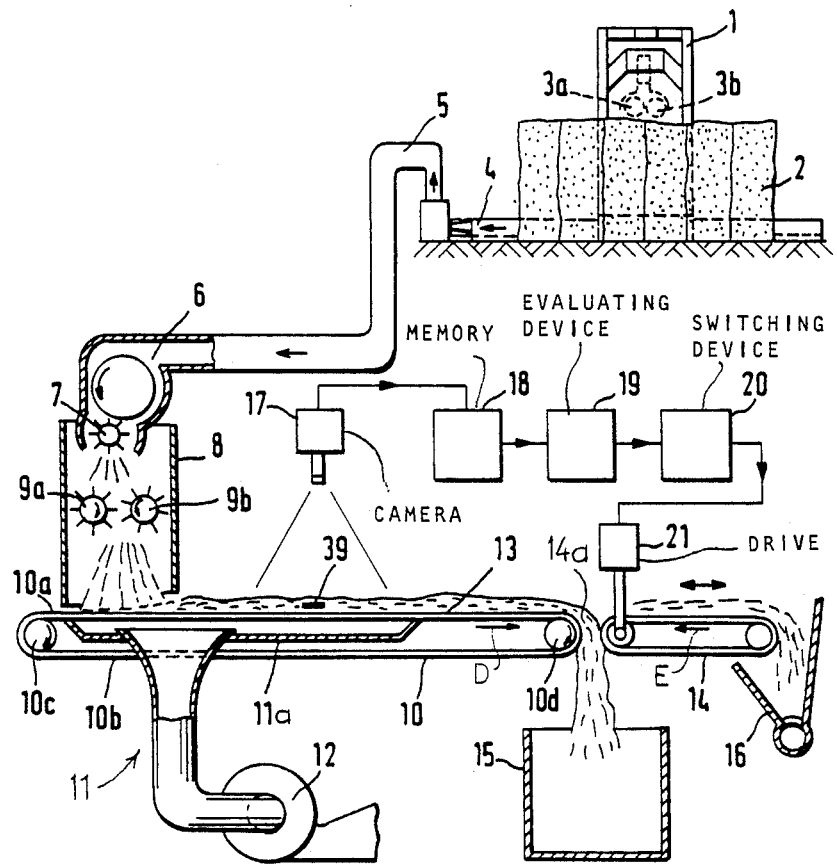
FIG. 1 is a schematic side elevational view, with block diagram, showing a preferred embodiment of the invention.

Turning to FIG. 1, there is illustrated a travelling bale opener 1 which includes opening rollers 3a, 3b for removing, during the travel of the bale opener, fiber tufts from the top faces of serially arranged fiber bales 2. The bale opener may be a "BLENDOMAT BDT" model, manufactured by Trützschler GmbH & Co. KG, Mönchengladbach, Federal Republic of Germany. The fiber tufts are pneumatically conveyed through a channel 4 and a conveyor duct 5 to a condenser 6, downstream of which there is arranged a stripping roller 7. The condenser 6 is situated at the upper end of a fiber tuft fill chute 8 (fiber tuft feeding device) which includes two delivery rollers 9a, 9b.

Underneath the fill chute 8 there is situated a conveyor belt 10 which is constituted by a sieve belt. Between the upper reach 10a and the lower reach 10b of the conveyor belt 10 there is situated a suction device 11 by means of which the upper reach 10a is exposed to suction from below. The suction device 11 comprises a shroud assembly 11a and a blower 12 connected at its suction side to the shroud assembly 11a. The loose fiber tuft mass 13 (layer) on the upper belt reach 10a has a relatively small thickness. Downstream of the conveyor belt 10 there is arranged a further conveyor belt 14. Between the two conveyor belts 10 and 14 a clearance 14a is present, underneath which a waste collector 15 is provided. At that end of the conveyor belt 14 which is remote from the conveyor belt 10 there is situated a suction device 16 for removing the fiber tufts.

Above the upper reach 10a of the conveyor belt 10 there is arranged a picture taking device, such as a television camera 17 oriented towards the fiber tuft mass 13. The camera 17 applies signals to an image storing device 18, an image evaluating device 19 for distinguishing foreign bodies from fiber tufts and a switching device 20 which, in turn, is connected with the drive motor 21 for the conveyor belt 14.

In operation, the tuft fill chute 8 scatters the fiber material as fiber tufts in a downward direction over a width of approximately 1 meter. Underneath this fiber tuft delivering station there is situated the conveyor belt (sieve belt) 10 which is exposed to a vacuum by the suction device 11. The conveyor belt 10 is driven by means of rollers 10c and 10d in a direction indicated by the arrow D. The speed of the non-illustrated motor for driving the conveyor belt 10 (for example, by virtue of rotating the roller 10c) is variable. By means of this apparatus, there is obtained a relatively uniform fiber tuft mass 13 whose density (thickness) may be adjusted in a desired manner by altering the travelling speed of the conveyor belt 10. The suction effect of the blower 12 provides that the fiber tufts of the fiber tuft mass 13 are compressed and thus the upper face of the fiber tuft layer is reduced and further, during the travel of the conveyor belt 10 there will be no appreciable relative velocities between the upper reach (conveying surface) 10a of the conveyor belt 10 and the fiber tufts of the fiber tuft layer 13.

The camera 17 monitors from above an approximately square zone and takes pictures which are stored in the memory 18. The sequence of picture taking by the camera corresponds to the belt speed such that each time a new layer portion arrives in the entire range of the camera 17 the subsequent picture will be taken thereby. The image evaluating device 19 detects any foreign body, such as foreign fibers. Downstream of the conveyor belt 10 there is arranged the additional conveyor belt 14 whose drive 21 is connected to the switching device 20, which at a predetermined moment after a foreign body was detected by the evaluating device 19, causes reversal of the conveyor belt 14 into the direction E. In this manner, the fiber mass 13, containing the foreign bodies 39 may be deflected downwardly into the waste container 15.

Figure 2:
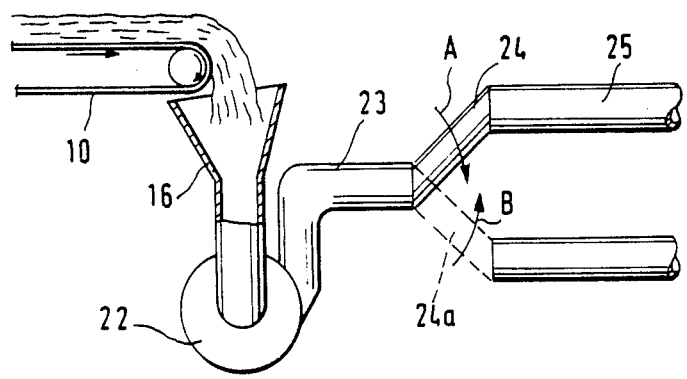
FIG. 2 is a schematic side elevational view, partially in section, of components of a further preferred embodiment of the invention.

Turning now to FIG. 2, downstream of the conveyor belt 10 there is arranged a suction device 16' which is, in turn, connected with a conveyor duct 23 with the intermediary of a fiber tuft driving fan 22. With the conveyor duct 23 there is connected a tubular switch (deflector tube) 24 which is connected with the electric switching device 20, arranged as shown in FIG. 1. When the evaluating device 19 determines the presence of a foreign body 39 in the fiber material 13, the switching device 20 emits a signal which is applied to the non-illustrated driving device for the tubular switch 24 which, in response, pivots in the direction of the arrow A into the position 24a shown in phantom lines. In this manner, the fiber material, containing the foreign bodies 39 is caused to follow a detour. Subsequently, the tubular switch 24 is pivoted back into its normal, solid-line position in the direction of the arrow B to ensure that the fiber material now free from foreign bodies may follow its normal path to further processing.

Figure 3:
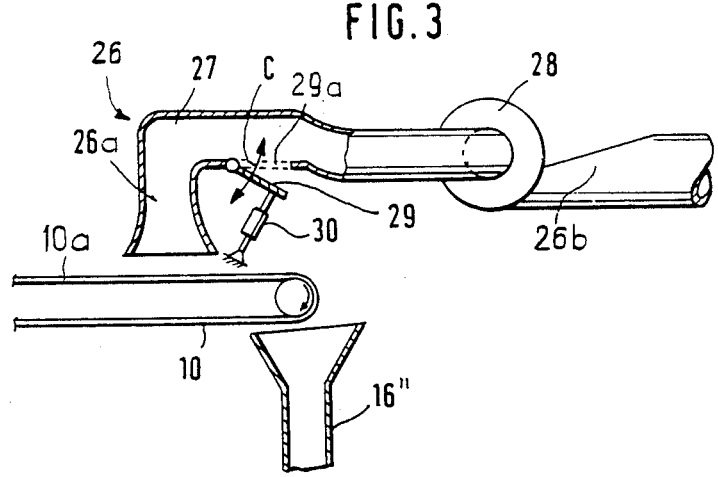
FIG. 3 is a schematic side elevational view, partially in section, of components of still another preferred embodiment of the invention.

Turning now to FIG. 3, above the downstream end of the upper reach 10a of the conveyor belt 10 there is provided a suction device 26 which, by means of the blower 28, lifts the fiber tufts off the conveyor belt 10 through the suction nozzle 26a and normally drives the fiber material into the duct 26b for further processing. For this operation a pivotal gate 29 is in its closed position shown in phantom lines at 29a. When the device 19 detects a foreign body 39 in the fiber material 13, the switching device 20 applies a signal to the actuating means 30 which pivots the gate 29 downwardly as indicated by the double-headed arrow C into its open position whereby the fiber material is taken out of the conduit 27 and introduced into a waste duct 16".

Turning now to the embodiment illustrated in FIG. 4, downstream of the discharge (delivering) rollers 9a and 9b there is arranged an opening roller 9c which directs the fiber tufts onto the upper reach 10a of the belt 10. Above the upper reach 10a there is situated a transmitting device 31 for emitting electromagnetic waves or rays, such as an X-ray apparatus. Between the upper reach 10a and the lower reach 10b of the conveyor belt 10 there is situated a receiver 32. The material of the conveyor belt 10 is pervious to electromagnetic irradiation. In this embodiment the loose fiber tuft layer 13 is traversed by irradiation. To the receiver 32 there are connected an image storing device 18, an image evaluating device 19, a signal transmitter 34 and a switching device 20, the latter being operatively coupled with a device for removing portions of the fiber tuft material containing the detected foreign body, as described in connection with the mechanisms shown in FIGS. 1, 2 and 3.

Turning to the embodiment illustrated in FIG. 5, there is shown a camera 17 arranged above the conveyor belt 10. With the end roller 10d supporting the conveyor belt 10 there cooperates a reversing device 35 for the fiber tuft layer 13, formed of an endless belt 36 supported by rollers 37a–37d driven in a direction opposite to the direction of rotation of the rollers 10c and 10d supporting the conveyor belt 10. At the downstream end of the conveyor belt 10 the fiber material 13 is grasped by the upper face 36a of the belt 36 as it cooperates with that portion of the conveyor belt 10 which is momentarily supported by the end roller 10d. Between a deflecting roller 38 and an end roller 37d the belt 36 has a horizontal belt portion 36a above which there is situated a further camera 17'. By virtue of the reversing device 35, at the downstream end of the upper reach 10a of the belt conveyor 10 the advanced fiber layer 13 is turned upside down to permit, by the camera 17', an observation of that side of the layer 13 which was the bottom side on the conveyor 10. The camera 17' may be connected to the devices 18, 19 and 20, similarly to the camera 17 associated with the conveyor belt 10.

It will be understood that the above description of the present invention is susceptible to various modifications, changes and adaptations, and the same are intended to be comprehended within the meaning and range of equivalents of the appended claims.

What is claimed is:

1. An arrangement for ascertaining the presence of foreign bodies in, and their removal from a mass of fiber tufts, comprising
   (a) a conveyor having a fiber tuft supporting surface;
   (b) means for forming a loose fiber tuft layer on said surface;
   (c) driving means for advancing the conveyor for moving the loose fiber layer in a conveying direction;
   (d) a foreign body detecting apparatus arranged for scanning the fiber tuft layer for ascertaining a presence of a foreign body at a first location and including signal generating means for generating a signal upon ascertaining said presence; and
   (e) a foreign body removing means operatively connected to said signal generating means for removing the foreign body at a second location upon receipt of said signal; said second location being downstream of said first location as viewed in said conveying direction.

2. An arrangement as defined in claim 1, wherein said conveyor belt is a generally horizontally oriented sieve belt; further comprising suction means situated underneath said surface for exposing said surface to suction from below.

3. An arrangement as defined in claim 2, wherein said means for forming a loose fiber tuft layer comprises a vertical fiber tuft feeder arranged above said fiber tuft-supporting surface.

4. An arrangement as defined in claim 1, wherein said foreign body detecting apparatus comprises means for ascertaining the configuration of the foreign body.

5. An arrangement as defined in claim 1, wherein said foreign body detecting apparatus comprises means for ascertaining the color of the foreign body.

6. An arrangement as defined in claim 1, wherein said foreign body detecting apparatus comprises means for ascertaining the size of the foreign body.

7. An arrangement as defined in claim 1, wherein said foreign body detecting apparatus comprises means for ascertaining the brightness of the foreign body.

8. An arrangement as defined in claim 1, wherein said foreign body detecting apparatus comprises a transmitter of electromagnetic waves facing one side of the fiber tuft layer, a receiver facing another, opposite side of the fiber tuft layer for receiving the electromagnetic waves passing through the fiber tuft layer.

9. An arrangement as defined in claim 8, wherein said foreign body detecting apparatus is an X-ray apparatus.

10. An arrangement as defined in claim 1, wherein said foreign body detecting apparatus comprises a picture-taking device.

11. An arrangement as defined in claim 10, wherein said picture-taking device comprises a television camera.

12. An arrangement as defined in claim 10, wherein said foreign body detecting apparatus further comprises an image storing device connected to said picture-taking device.

13. An arrangement as defined in claim 12, wherein said foreign body detecting apparatus further comprises an evaluating device connected to said image storing device for differentiating foreign bodies from fiber tufts.

14. An arrangement as defined in claim 13, wherein said foreign body removing means is connected to said evaluating device for receiving said signal from said evaluating device upon detection of a foreign body thereby.

15. An arrangement as defined in claim 13, further wherein said conveyor has a face constituting said fiber tuft-supporting surface; further comprising receiving means for receiving the fiber layer from a discharge end of said conveyor belt and for advancing the fiber tufts for further processing; said foreign body removing means comprising re-routing means operatively connected to said evaluating device and said conveyor belt for deviating said fiber tuft layer from said receiving means upon a signal from said evaluating device for preventing a detected foreign body from being advanced for said further processing.

16. An arrangement as defined in claim 15, wherein said re-routing means includes an additional conveyor belt adjoining said discharge end at a clearance therefrom; said additional conveyor belt being situated between said discharge end and said receiving means; further comprising driving means operatively connected to said evaluating device and said additional conveyor belt for driving said additional conveyor belt in a first direction in the absence of a foreign body detection signal from said evaluating device and for driving said additional conveyor belt in a second direction in response to a foreign body detection signal from said evaluating device; when driven in said first direction, said additional conveyor belt advancing the fiber tuft layer from said discharge end to said receiving means and when driven in said second direction, said additional conveyor belt causing discharge of said fiber tuft layer through said clearance, circumventing said receiving means.

17. An arrangement as defined in claim 1, wherein said conveyor comprises a first conveyor belt having a first face constituting one part of said fiber tuft supporting surface and an end roller supporting said first conveyor belt and defining a discharge end thereof; a second conveyor belt having a second face constituting another part of said fiber tuft-supporting surface; said second face cooperating with said first face at said discharge end for transferring the fiber tuft layer from said first face of said first conveyor to said second face of said second conveyor such that the top and bottom of the fiber tuft layer are reversed on said second conveyor belt as compared to the first conveyor belt; further wherein said foreign body detecting apparatus comprises a first detecting device arranged for scanning the fiber tuft layer on said first conveyor belt and a second detecting device arranged for scanning the fiber tuft layer on said second conveyor belt.

* * * * *